(12) United States Patent
Gillig et al.

(10) Patent No.: US 9,324,552 B2
(45) Date of Patent: Apr. 26, 2016

(54) PERIODIC FIELD DIFFERENTIAL MOBILITY ANALYZER

(71) Applicant: Academia Sinica, Taipei (TW)

(72) Inventors: Kent J. Gillig, Taipei (TW); Chung-Hsuan Chen, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/713,792

(22) Filed: Dec. 13, 2012

(65) Prior Publication Data

US 2013/0187042 A1 Jul. 25, 2013

Related U.S. Application Data

(60) Provisional application No. 61/576,165, filed on Dec. 15, 2011.

(51) Int. Cl.
| | |
|---|---|
| *H01J 49/28* | (2006.01) |
| *G01N 27/62* | (2006.01) |
| *H01J 49/26* | (2006.01) |
| *H01J 49/22* | (2006.01) |
| *H01J 49/00* | (2006.01) |

(52) U.S. Cl.
CPC ............. *H01J 49/26* (2013.01); *G01N 27/624* (2013.01); *H01J 49/0031* (2013.01); *H01J 49/22* (2013.01)

(58) Field of Classification Search
CPC ............................ H01J 49/443; H01J 49/446
USPC .................................................. 250/256, 287
See application file for complete search history.

(56) References Cited

U.S. PATENT DOCUMENTS

| | | | |
|---|---|---|---|
| 4,900,974 A | 2/1990 | Ishitani | |
| 5,621,208 A * | 4/1997 | Pourprix | G01N 15/0266 250/281 |
| 2003/0116708 A1 | 6/2003 | De La Mora | |
| 2005/0173629 A1 * | 8/2005 | Miller et al. | 250/290 |
| 2006/0192102 A1 | 8/2006 | Miller | |
| 2006/0192103 A1 * | 8/2006 | Landgraf | 250/287 |
| 2007/0044580 A1 * | 3/2007 | Arcas et al. | 73/865.5 |
| 2008/0017795 A1 * | 1/2008 | Ramiro Arcas | H01J 49/40 250/294 |
| 2009/0189069 A1 * | 7/2009 | Chen et al. | 250/282 |
| 2010/0282961 A1 * | 11/2010 | Miller et al. | 250/282 |
| 2011/0133076 A1 | 6/2011 | Miller | |

(Continued)

FOREIGN PATENT DOCUMENTS

WO WO 2011071182 A1 * 6/2011

OTHER PUBLICATIONS

Loscertales, Drift Differential Mobility Analyzer, J Aerosol Sci., vol. 29, ppl 117-1139, 1998.*

(Continued)

*Primary Examiner* — Jack Berman
*Assistant Examiner* — James Choi
(74) *Attorney, Agent, or Firm* — Eckman Basu LLP

(57) ABSTRACT

A periodic field differential mobility analyzer apparatus for separating and identifying ionic analytes employs a series of elongated parallel channels, a pump, a first voltage providing an electric field $E_x$ in a direction opposing the gas flow, a second voltage providing an electric field $E_y$ in a direction perpendicular to the gas flow, an ion source, and a detector. The periodic field differential mobility analyzer provides high resolution and sensitivity.

36 Claims, 15 Drawing Sheets

(56) References Cited

U.S. PATENT DOCUMENTS

2012/0001067 A1* 1/2012 Orii et al. .................. 250/288
2012/0248303 A1* 10/2012 Hiraoka .................... 250/282
2015/0115147 A1* 4/2015 Oberreit ............... G01N 27/622
                                                      250/282

OTHER PUBLICATIONS

Tammet, The Limits of Air Ion Mobility Resolution, Proc. 11th Int. Conf. Atmos. Electr., NASA, MSFC, Alabama, 626-629, 1999.*

* cited by examiner

US 9,324,552 B2

PERIODIC FIELD DIFFERENTIAL MOBILITY ANALYZER

TECHNICAL FIELD OF THE INVENTION

This invention relates to the fields of ion mobility spectrometry and ion analysis. In particular, this application relates to methods for separation and identification of ions, molecules and particles. More particularly, this application relates to an apparatus and methods for separation and analysis of ions by differential mobility with a periodic field.

BACKGROUND OF THE INVENTION

Ion Mobility Spectrometry (IMS) is a technique that separates ions in terms of their mobility with reference to a drift/buffer gas. The analysis is based on measuring the velocity which gaseous ions attain while drifting a defined distance through the buffer gas. Prior art mobility techniques are known as "time-of-flight" separation techniques if based on time or as "differential" separation techniques if ion detection is based on position. Drift-tube mobility analyzers operate by recording the time-of-flight of ion packets separated by their mobility in a background gas under the influence of a uniform electric field. The background gas is introduced at a low flow rate in the opposite direction.

A differential mobility analyzer (DMA) operates by combining the perpendicular forces of a flowing gas and an electric field. The diffusion limited resolution attainable with a TOF analyzer is substantially higher than typical DMA values but DMAs attain higher sensitivities by virtue of the continuous ion beam analyzed (a factor of ~100 because of the low duty cycle of TOF analyzers). One disadvantage of TOF mobility analyzers is that the particles/ions are not easily selected according to their mobility. Additional ion gates can be employed but aliasing of the mobility due to multiples of the period and the low resulting duty cycle make that type of instrument unreliable and inadequate for mobility selection. In contrast, a DMA instrument is naturally useful for mobility selection providing a continuous stream of ions of one size that can then be directed toward other instruments/analyzers i.e. mass spectrometer, optical spectrometer, ion trap, surface (soft-landing, dissociation), etc.

There are three factors that adversely influence the motion of ions in a prior art DMA: (1) dilution by mixing of the inlet flow and sheath gas flow, (2) ion diffusion (Brownian motion), and (3) finite slit width A theoretical value of resolution (R) calculated as a Gaussian-type transfer function with full width $\Delta Z$ at half-height can be approximated as a summation of the square of the variances due to these three factors as in Equation 1

$$\left(\frac{Z}{\Delta Z}\right)^2 = \left(\frac{Q_{sh}}{Q_{in}}\right)^2 + \frac{Pe}{16\ln2(b+b^{-1})G(y_i)} + \left(\frac{L}{2\Delta L}\right)^2 \quad \text{Equation 1}$$

where Z is the particle/ion mobility, $Q_{sh}$ is the sheath gas flow rate, $Q_{in}$ is the inlet gas flow rate, $G(y_i)$ and b are dimensionless geometry factors, Pe is the Peclet number (a dimensionless engineering parameter related to x, y, z), L is the axial length from entrance to exit slit, and $\Delta L$ is the exit slit width (See H. Tanaka, K. Takeuchi, Aerosol Science, (2003) vol. 34, 1167-1173).

To obtain higher resolution, a DMA should be operated at higher gas flow velocities (high Reynolds or Peclet numbers) and at subsequently higher voltages (first terms on the right, and the $Z/\Delta Z$ term, in Equation 1, respectively) (See J. F. de la Mora, L. de Juan, T. Eichler, J. Rosell, Trends in Anal. Chem., (1998) vol. 17, 6, 328-338). In turn, the pumps required to obtain high gas flow velocities become larger as the inlets are better designed to create laminar flow. Typical commercially available aerosol DMAs can obtain a resolution from 1 to ~10. For example, the TSI Inc. Particle Sizer Spectrometers operate with ($Q_{sh}/Q_{in}$) equal to 4, limiting the resolution to <4. (Model 3091 Fast Mobility Particle Sizer Spectrometer, 2004; Model 3034 Scanning Mobility Particle Sizer, 2003) Higher performance research instruments of "unusually high resolution", in practice typically operate at a resolution <25 because of high inlet flow rates and extremely narrow (<0.1 mm) exit slits requiring pumping speeds up to 3000 l/min. These factors limit the resolution of prior art DMAs severely and the highest reported resolution of 60 required a Reynolds number approaching 100000. These pumping requirements are impractical; therefore a new DMA design is needed.

FIG. 1 shows a schematic of a prior art DMA common to the field in which mobility separation is obtained by using two planar plates (A and B) between which a laminar gas flow ($Q_{sh}$), and a scanning voltage (E) are applied. Charged particles/ions for analysis are introduced with $Q_{in}$ and are detected by an electrometer. The operating principle and range of use is basically identical to that of the cylindrical DMA, the difference being only that the electric field is uniform between the two plates whereas the field inside the cylindrical DMA is increasing (in absolute value) toward the center electrode. Various attempts have been made to improve DMA performance including inversion of the direction of particle paths and reductions of the length to gap ratio. In particular, a number of attempts have been made to vary the electric field configuration with respect to the gas flow following a design originally proposed by Loscertales. (See Loscertales, "Drift Differential Mobility Analyzer", Journal of Aerosol Science, 1998, 29, 1117-1139) These attempts include the "Inclined Grid" method of Tammet (See Tammet, "The Limits of Air Ion Mobility Resolution", Proc. 11th Int. Conf. Atmos. Elect., NASA, MSFC, Alabama, 1999, 626-629), the various configurations of Labowsky and De La Mora (WO2004/077016 A2), the "Cross-Flow Differential Migration Classifier" of Flagan (U.S. Pat. App. 2004/0050756 A1), and the cylindrical "Cross-Flow Ion Mobility Analyzer" of Rockwood et. al. (U.S. Pat. App. 2005/0006578 A1) All of these methods change the geometry factor of cylindrical or planar devices and the increase in resolution is determined by the amount of electrical work done with respect to the gas flow but also by the other factors in equation 1. Those factors may limit or even decrease the overall resolution. In practice the only significant improvement in resolution has involved increasing the gas flow rate, an exception being the device of Gillig et al., a Multislit-Multigap DMA (MMDMA) consisting of a series of DMAs where the ions pass through a series of small slits, reducing the pumping requirements and improving the resolution by maintaining laminar flow at high gas velocities. (See K. J. Gillig, R. Sperline, M. B. Denton, Multi-slit/Multi-channel Differential Mobility Analyzer, Pittcon 2007, Chicago, Ill., USA) A schematic of a MMDMA is shown in FIG. 2.

There is a continuing need for methods to reduce the pumping requirements in ion mobility spectrometry and differential mobility analysis. There is also a need for an apparatus and arrangement for mobility spectrometry and analysis to obtain high resolution and identification of analytes.

BRIEF SUMMARY OF THE INVENTION

This invention provides a periodic field differential mobility analyzer (PFDMA) that employs a series of single stage reversed field differential mobility analyzers operating simultaneously in tandem in a periodic mode. The periodic field differential mobility analyzer of this invention achieves separation with increased resolution by increasing the amount of electrical work done with respect to the gas flow.

The periodic field differential mobility analyzer of this invention achieves separation with increased resolution with an overall pumping speed that is reduced by a factor equal to or approaching the number of individual single stage reversed field differential mobility analyzers employed in the apparatus.

In some embodiments, this invention provides methods and apparatuses for the separation and analysis of ions, comprising (a) an ionization source to generate ions, (b) a PFDMA coupled to the ionization source in which ions are separated according to their mobility, and which includes a series of differential mobility analyzers arranged in a manner such that a periodic field is formed, and arranged in sequential combination for transport, and (c) an ion detector for simultaneous measurement.

Each of the series of differential mobility analyzers can operate by sweeping a voltage across the differential mobility analyzer to select/scan a mobility range that is sampled through an exit aperture/slit.

In some aspects, the periodic field differential mobility analyzer of this invention achieves increased resolution for analytes using a series of differential mobility analyzers by applying a linearly increasing voltage across the composite PFDMA or space offset, along with simultaneous selection/sweeping of the total voltage, and recirculation of the gas flow to each analyzer of the series. High resolution can be achieved due to the increase in the amount of work on the ion analytes, while the ion transmission remains high because of the periodic nature of the increasing/decreasing electric fields.

In further aspects, the device can either be operated with a large pump to obtain a high gas velocity, or in a circulating mode where the pumping requirements are reduced by a factor equal to the number of individual channels which is the number of differential mobility analyzers in the series.

In alternative embodiments of the invention, individual channels can be construction to form uniform or non-uniform electric fields, or there can be superposition of static or dynamic electric fields, or replacement of gas flow and electric fields with other force fields, for example, magnetic, thermophoretic, centrifugal, gravitational, and photophoretic fields.

This invention includes a periodic field differential mobility analyzer apparatus for separating and identifying ionic analytes, comprising:

a series of elongated parallel channels, each channel having an inlet at a first end and an outlet at a second end, each channel enclosed between first and second parallel walls, each first wall being formed from first and second electrode plates arranged to provide a slit opening in the first wall, each second wall being formed from third and fourth electrode plates arranged to provide a slit opening in the second wall, wherein the first and third electrode plates enclosing a channel oppose each other and the second and fourth electrode plates enclosing a channel oppose each other, wherein adjacent channels share electrode plates of one wall in common, wherein the channels are in fluid communication through the slit openings in each wall, and wherein the slit openings in each of the channels are aligned;

a pump operable to force gas in laminar flow along each of the series of parallel channels;

a first voltage drop applied between the first and second electrode plates of the first wall of each channel providing an electric field $E_x$ in a direction opposing the gas flow, wherein the first voltage drop is also applied between the third and fourth electrode plates of the second wall;

a second voltage drop applied between the first and third electrode plates of each channel providing an electric field $E_y$ in a direction perpendicular to the gas flow, wherein the second voltage drop is also applied between the second and fourth electrode plates of each channel, wherein the electric fields $E_x$ and $E_y$ form a periodic arrangement of their combined electric field and a retarding potential wall;

an ion source arranged exterior to the channels for directing ionic analytes into a slit of the wall of the channel farthest upstream with respect to the electric field $E_y$; and a detector.

In some embodiments, the analyzer further includes an exit slit in the wall of the channel farthest downstream with respect to the electric field $E_y$.

The analyzer may include means for recirculating gas exiting from a channel into the inlet of a channel downstream with respect to the electric field $E_y$, or means for recirculating gas exiting from each channel into the inlet of an adjacent channel downstream with respect to the electric field $E_y$.

In certain embodiments, the slit openings in each of the channels are aligned in a direction perpendicular to the walls of the channels.

The detector can be downstream from the ion source with respect to the direction of gas flow, wherein the slit openings in each of the channels are aligned in a predetermined angle relative to the direction perpendicular to the walls of the channels.

In some embodiments, the analyzer may include maintaining the first and third electrode plates of each channel at ground potential, wherein the detector is downstream from the ion source with respect to the direction of gas flow, and wherein the slit openings in each of the channels are aligned in a predetermined angle relative to the direction perpendicular to the walls of the channels.

In certain embodiments, the detector can be upstream from the ion source with respect to the direction of gas flow, and wherein the slit openings in each of the channels are aligned in a predetermined angle relative to the direction perpendicular to the walls of the channels.

An analyzer may have any number of channels in the series of elongated parallel channels. In some embodiments, an analyzer may have a number of channels in the series of elongated parallel channels from two to twenty, or from two to thirty, or from two to forty, or from two to fifty, or from two to seventy, or from 2 to 100.

In some aspects, the first voltage drop can be swept from zero to 2000 volts.

In certain aspects, the pump may be operable to adjust the gas flow rate, for example, from 0.1 to 2500 L/min, or from 1 to 1000 L/min, or from 1 to 2500 L/min, or from 1 to 5000 L/min. The pump may be operable to provide a gas flow rate of at least 500, 750, 1000, 1250, 1500, 2000, 2500, 3000, 4000 or 5000 L/min.

The gas flow rates in each of the channels may be equal or unequal. In some embodiments, the gas flow rates in each of the channels are equal.

The ion source can generate ions by MALDI, electrospray ionization, laser ionization, thermospray ionization, thermal ionization, electron ionization, chemical ionization, inductively coupled plasma ionization, glow discharge ionization, field desorption ionization, fast atom bombardment ionization, spark ionization, or ion attachment ionization. The ion source can be a voltage biased tungsten wire.

In some embodiments, the detector is a current to voltage converter, a gas amplification detector, a Daly detector, or a charge detector.

In some aspects, the analyzer can achieve a resolution of greater than 100 with a transmission of greater than 90%, or a resolution of greater than 200 with a transmission of greater than 40%, or a resolution of greater than 50, or a resolution of greater than 75, or a resolution of greater than 100, or a resolution of greater than 200.

In further aspects, an analyzer above may be incorporated into a mass spectrometer.

In further aspects this invention provides a periodic field differential mobility analyzer apparatus for separating and identifying ionic analytes, comprising:

a series of differential mobility analyzers having channels arranged in parallel, wherein adjacent differential mobility analyzers share a common wall;

a pump operable to force gas in laminar flow along the channels;

a first voltage drop applied to each differential mobility analyzer to provide an electric field $E_x$ in a direction opposing the gas flow;

a second voltage drop applied to each differential mobility analyzer to provide an electric field $E_y$ in a direction perpendicular to the gas flow, wherein the electric fields $E_x$ and $E_y$ form a periodic arrangement of their combined electric field and a retarding potential wall;

an ion source arranged exterior to the channels for directing ionic analytes through a slit of the wall of the channel farthest upstream with respect to the electric field $E_y$; and a detector.

This invention further contemplates methods for separating and identifying ionic analytes, the method comprising providing a series of elongated parallel channels, each channel having an inlet at a first end and an outlet at a second end, each channel enclosed between first and second parallel walls, each first wall being formed from first and second electrode plates arranged to provide a slit opening in the first wall, each second wall being formed from third and fourth electrode plates arranged to provide a slit opening in the second wall, wherein the first and third electrode plates enclosing a channel oppose each other and the second and fourth electrode plates enclosing a channel oppose each other, wherein adjacent channels share electrode plates of one wall in common, wherein the channels are in fluid communication through the slit openings in each wall, and wherein the slit openings in each of the channels are aligned; operating a pump to force gas in laminar flow along each of the series of parallel channels; applying a first voltage drop between the first and second electrode plates of the first wall of each channel providing an electric field $E_x$ in a direction opposing the gas flow, wherein the first voltage drop is also applied between the third and fourth electrode plates of the second wall; applying a second voltage drop between the first and third electrode plates of each channel providing an electric field $E_y$ in a direction perpendicular to the gas flow, wherein the second voltage drop is also applied between the second and fourth electrode plates of each channel, wherein the electric fields $E_x$ and $E_y$ form a periodic arrangement of their combined electric field and a retarding potential wall; directing ionic analytes from an ion source into a slit of the wall of the channel farthest upstream with respect to the electric field $E_y$; and detecting the ionic analytes.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, or limited to any preferred embodiments, and the scope of the present invention is defined by the appended claims.

BRIEF DESCRIPTION OF THE DRAWINGS

In FIG. 6, the conditions were m/z 250, 760 Torr air, 7.5 mm total length, 2 kV total voltage drop.

FIG. 8A shows ion trajectories when the voltage is too low to create a complete retarding wall. FIG. 8B shows ion trajectories when the voltage is sufficient to create a complete retarding wall. FIG. 8C shows ion trajectories when the voltage is too high to create a complete retarding wall.

FIG. 10 shows ion mobility spectra obtained with a PFDMA.

FIG. 11 shows ion mobility spectra obtained with a PFDMA.

FIG. 12 shows ion mobility spectra obtained with a computer controlled PFDMA.

12a, but the source conditions produced larger acetone cluster ions. FIG. 12c shows an overlay ion mobility spectrum obtained using a six channel prototype PFDMA. The device was operating in a higher resolution mode, which was higher voltage and higher gas velocity than shown in FIG. 12a.

DETAILED DESCRIPTION OF THE INVENTION

Embodiments of this invention provide novel methods for separation and identification of ions, molecules and particles. In some aspects, this disclosure provides an apparatus and methods for separation and analysis of ions by differential mobility with a periodic field.

Figure 1:
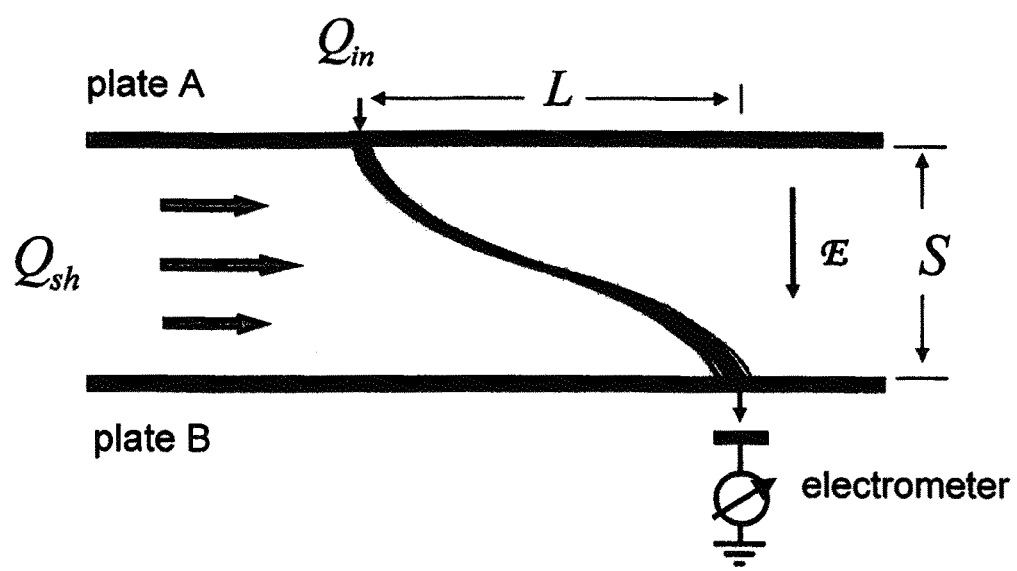
FIG. 1 shows a schematic of a prior art planar Differential Mobility Analyzer.
Figure 2:
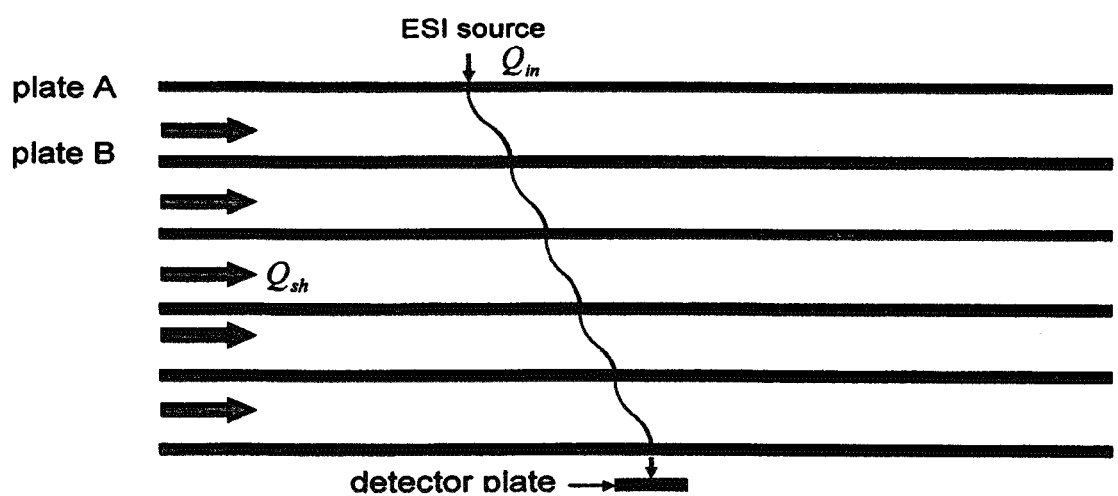
FIG. 2 shows a schematic of a prior art Multi-Slit/Multi-Gap Differential Mobility Analyzer.
Figure 3:
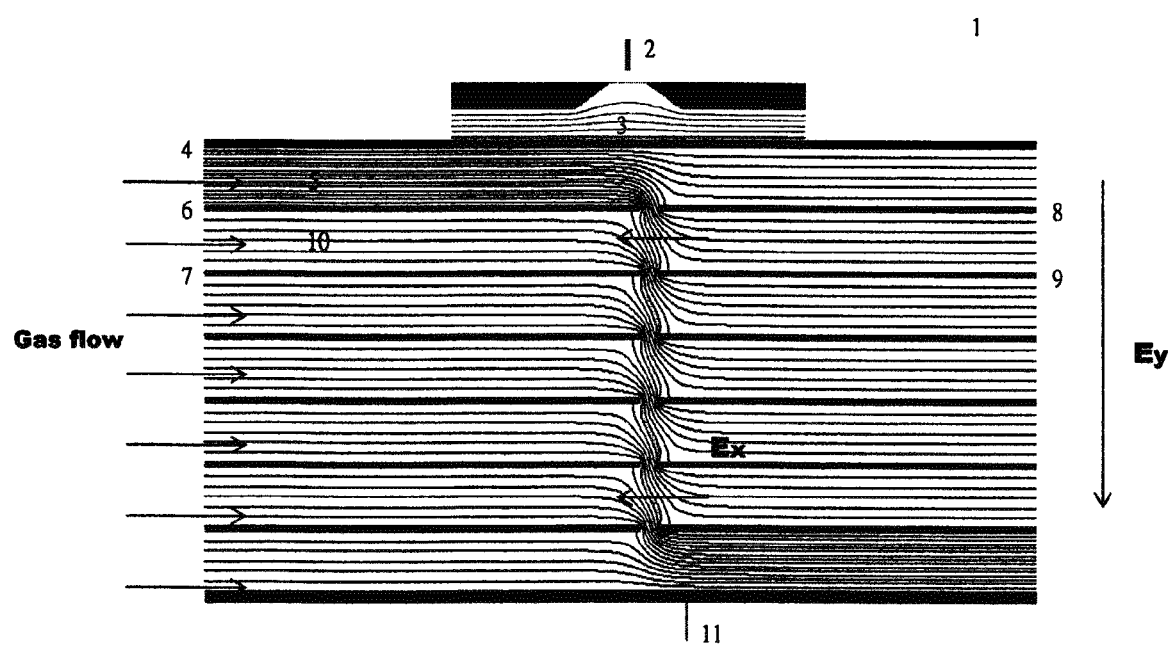
FIG. 3 shows a schematic of an embodiment of a Periodic Field Differential Mobility Analyzer of this invention.

FIG. 3 shows a schematic of an embodiment of a Periodic Field Differential Mobility Analyzer 1. An ion source 2 is arranged exterior to the entrance slit 3 into which a continuous ion beam is directed using a suitable arrangement of electric fields. The ion source is optimized so the inlet gas flow is minimized (factor 1 from Equation 1). Through entrance slit 3 ions enter channel 5 separated by plates (electrodes) 4 and 6, which constitute the first of a series of channels. In channel 5 the ions follow a trajectory determined by the perpendicular gas flow velocity, the voltage drop between plates 4 and 6, and the voltage drop between plates 6 and 8 (mobility dependent). After traversing channel 5 ions enter a periodic arrangement of electric fields formed by applying suitable voltages to two sets of plates. For example, a potential drop is applied between plates 6 and 7 and plates 8 and 9 forming the electric field Ey (perpendicular to the gas flow) while a potential drop applied between plates 8 and 6 and plates 9 and 7 forms the electric field Ex (opposing the gas flow).

Figure 4:
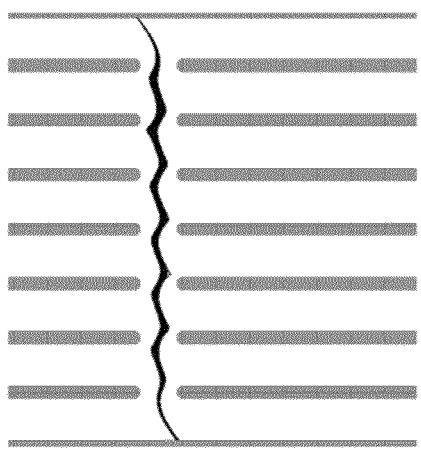
FIG. 4 shows a schematic of the retaining wall and periodic field effect in an embodiment of a Periodic Field Differential Mobility Analyzer (Common Voltage Analyzer).

FIG. 4 shows a schematic of an embodiment of a Periodic Field Differential Mobility Analyzer (Common Voltage Analyzer).

As shown in FIG. 4, a retarding potential wall is formed in the middle of the device along which ions are guided by a series of periodic electric fields perpendicular and in opposition to the gas flow.

FIG. 4 shows ion trajectories for m/z 250 ions from the source slit to the detector when Ex is low, which is a high transmission mode.

Figure 5:
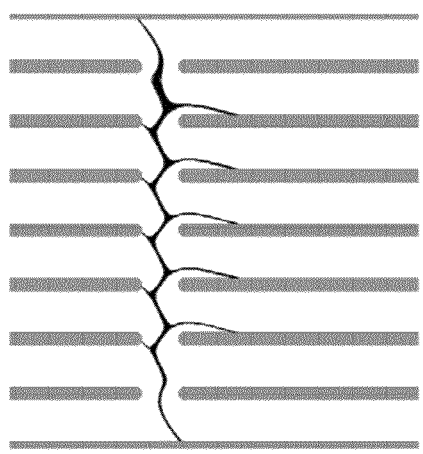
FIG. 5 shows a schematic of an alternate embodiment of a Periodic Field Differential Mobility Analyzer.

FIG. 5 shows ion trajectory calculations for m/z 250 ions when Ex is high, which is a high resolution mode.

For this embodiment of a Periodic Field Differential Mobility Analyzer, as the electric field Ex is increased, ions are squeezed between the two series of electrodes where there exists a periodic series of stagnation points. Decreasing the electric field strength in the Ex direction decreases the intensity of the stagnation points and ions are allowed to pass.

Figure 6:
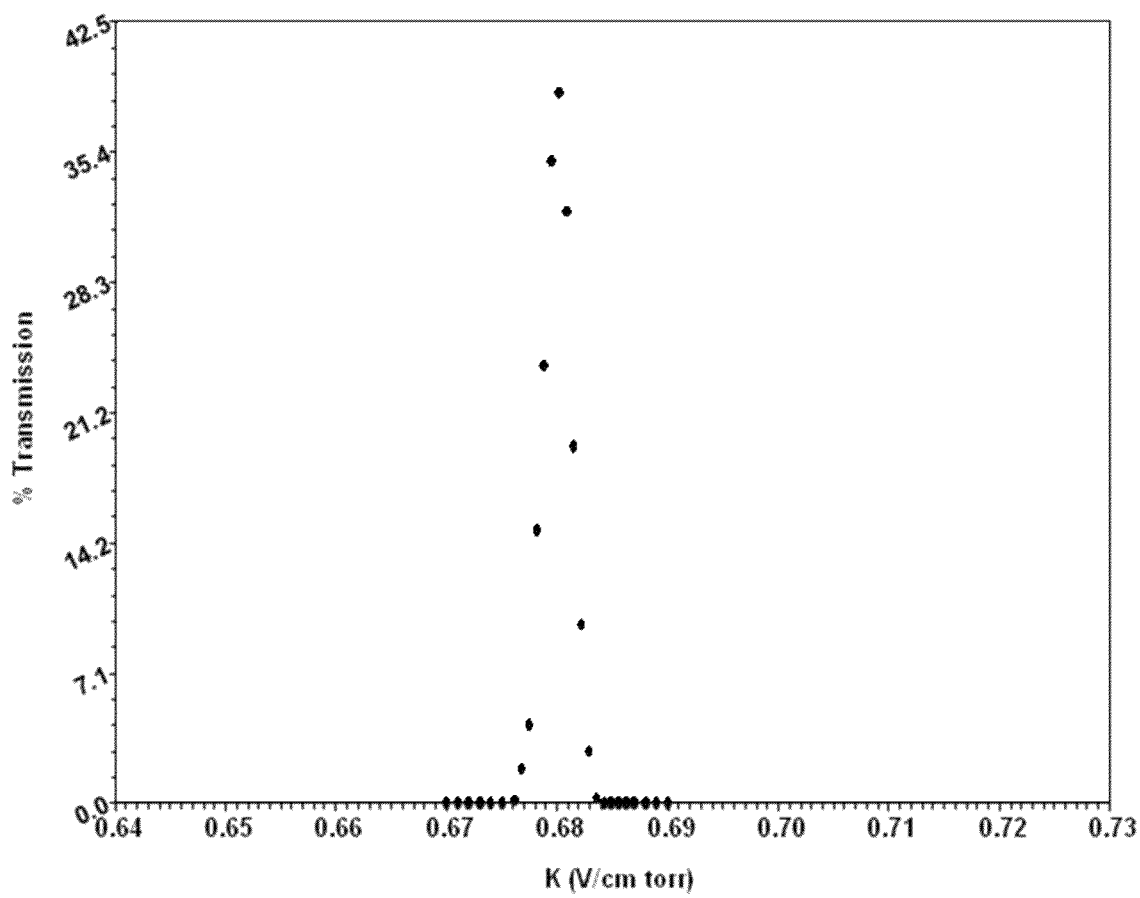
FIG. 6 shows a simulated ion mobility spectrum obtained from ion trajectory calculations.

As shown in FIG. 6, by sweeping the electric field strength Ex and recording the number of ions reaching the detector a simulated ion mobility spectrum was obtained. The ion trajectory calculations predict a very high resolution of >200 using modest voltages and flow rates. Note that the ion transmission is still over 40% and reducing the electric field/gas flow rate to obtain a resolution of ~100 results in 100% ion transmission.

In alternative embodiments of this invention, a retarding potential wall may be formed opposing the gas flow direction at a predetermined angle such that only one voltage is required.

Figure 7:
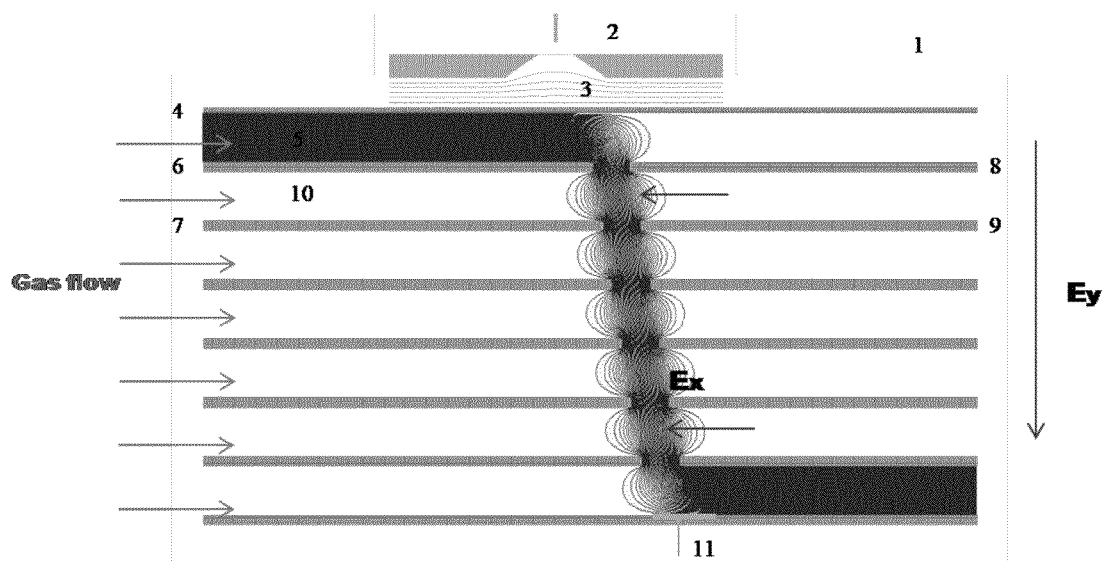
FIG. 7 shows a schematic of an embodiment of a Periodic Field Differential Mobility Analyzer (Common Voltage). The detector is downstream from the source.

FIG. 7 shows a schematic of an embodiment of a Periodic Field Differential Mobility Analyzer 1 (Common Voltage). An ion source 2 is arranged exterior to the entrance slit 3 into which a continuous ion beam is directed using a suitable arrangement of electric fields to enter channel 5 followed by channel 10. The embodiment shown in FIG. 7 differs from the PFDMA shown in FIG. 3 at least because only one voltage is applied to one series of electrodes in the embodiment shown in FIG. 7. For example, a common potential can be applied to plates 4, 8, and 9, while plates 6 and 7 are held at ground potential. Again, a retarding potential wall is formed opposing the gas flow direction, but at a predetermined angle such that only one voltage is required.

In FIG. 7, the plate farthest downstream with respect to the electric field $E_y$ can be used for detection, or can have an exit slit at location 11 to allow ionic analytes to exit to a detector.

The embodiment shown in FIG. 7 advantageous because a voltage can be selected and applied for which ions of a particular mobility range pass through the device to the detector. High mobility ions may be sampled further downstream of the original ion entrance. Higher sensitivity may be achieved by using all ions produced.

Figure 8:
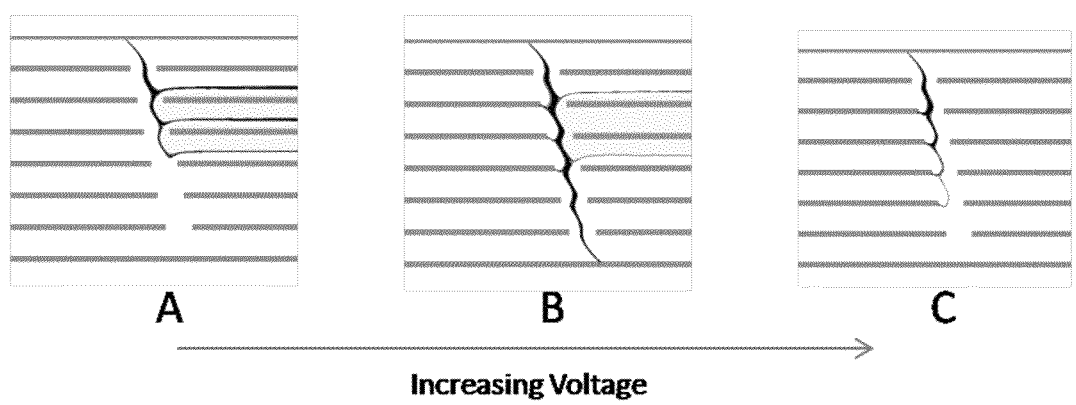
FIG. 8 shows ion trajectory calculations to illustrate the operating principle of the PFDMA arranged in a Common Voltage configuration.

Operation of the embodiment shown in FIG. 7 is illustrated in FIG. 8. FIG. 8 shows ion trajectory calculations to illustrate the operating principle of the PFDMA arranged in a Common Voltage configuration.

FIG. 8 shows ion trajectory calculations obtained at three different voltages: A, B, and C. Only when voltage B is applied can ions of a particular mobility range pass through the device to the detector. In addition, this common voltage device can be operated in a non-destructive mode where high mobility ions can be sampled further downstream of the original ion entrance. This configuration of multiple channels (array) would result in a much higher sensitivity by efficiently using all ions produced.

In further alternative embodiments, the electrodes may be arranged such that the detector is located upstream from the ion source. The advantage of this device is that even more work is done on the ions during passage implying that a higher resolution should be attainable at the same operating voltages applied to the inline device.

Figure 9:
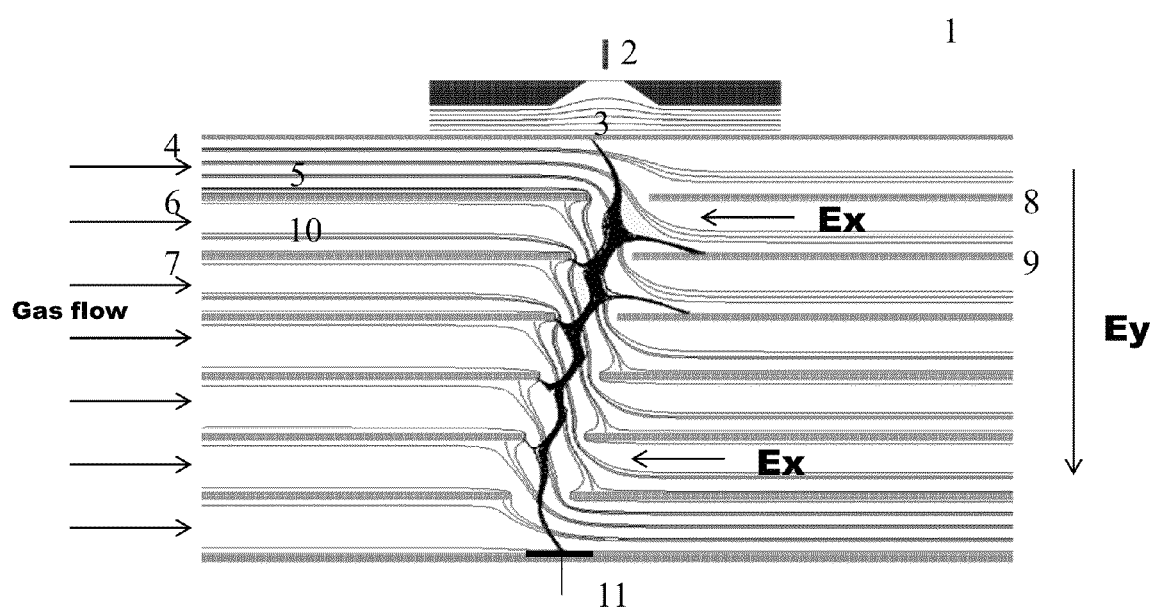
FIG. 9 shows a schematic of an alternate embodiment of a PFDMA where the detector is located upstream of the ionization source.

FIG. 9 shows a schematic of an alternate embodiment of a PFDMA 1 where the detector is located upstream of the ionization source. An ion source 2 is arranged exterior to the entrance slit 3 into which a continuous ion beam is directed using a suitable arrangement of electric fields to enter channel 5 followed by channel 10.

The embodiment shown in FIG. 9 differs from the PFDMA shown in FIG. 3 at least because the electrodes are arranged such that the detector is located upstream from the ion source. The advantage of this device is that even more work is done on the ions during passage implying that a higher resolution should be attainable at the same operating voltages applied to the inline device shown in FIG. 3.

In an alternative embodiment, the gas flow may be controlled in such a manner that gas exiting channel 5 on the right side of FIG. 3 is redirected to enter channel 10 on the left side of FIG. 3. This procedure of recirculation can be continued until the gas finally exits from the bottom channel on the right side of FIG. 3. The gas velocity in each channel/DMA is therefore increased by a factor equal to the number of channels (compared with the case where a fixed volume of gas passes in parallel through all channels) because they operate simultaneously as one long small cross section channel. In a preferred embodiment, the gas flow velocities in all the channels are equal, each plate being connected through an equal resistor chain (or computer controlled independent voltages are applied to each plate) so a linearly decreasing voltage (in absolute value) exists from the first to the last plate of each plate set which is biased near ground potential. The scanning potential can be applied to the higher potential set of plates across the resistor chain while a spectrum of ion intensity is recorded on a detector plate amplified by an electrometer. Additionally, the number of channels/plates/slits can be increased while high velocity laminar flow is easily maintained in each channel. A PFDMA can therefore be designed such that the total length from source slit to detector slit/resolution/total voltage drop is much greater than in existing single channel DMAs because the pump size required to maintain a high gas velocity is dependent only on the cross sectional area of one individual channel.

In FIG. 3, the plate farthest downstream with respect to the electric field $E_y$ can be used for detection, or can have an exit slit at location 11 to allow ionic analytes to exit to a detector.

Means for recirculating gas exiting from a channel include gas tubing and zig-zag gas channels.

By virtue of the PFDMA being a mobility spectrometer that can transmit a continuous stream ions of one size range, the coupling of a high resolution PFDMA to other instruments would be principally very useful. In particular, an ion trapping (quadrupole ion trap mass spectrometer or an ion cyclotron resonance mass spectrometer) device could accumulate size-selected ions and other analytical techniques could be applied to the size-selected ions, e.g., m/z identification, fragmentation, ion chemistry, and/or laser spectroscopy.

In a further embodiment, the channel size can be reduced to further reduce the required pumping speed for portability.

In an additional embodiment, the total number of channels can be increased to raise the resolution beyond that of current DMAs while using an equally sized or smaller pump. The gas may also be re-circulated in any combination of channels, or not be re-circulated in every channel, or the gas velocity itself may be varied to cover a wider ion size range.

In a further embodiment, different types of ion detectors may be used, for example, detectors based on gas amplification, mass spectrometers with post acceleration i.e. Daly detectors, or mass spectrometers with charge detection to increase the sensitivity of the basic PFDMA esp. for high m/z ions.

Example 1

A prototype PFDMA consisting of a pair of four 0.50 mm channels separated by 0.50 mm was constructed. The arrangement was similar to the schematic shown in FIG. 3, i.e. in an inline mode. The gas flow was produced using a common vacuum cleaner connected to a rheostat to set the velocity, drawn in from the surrounding laboratory air (unfiltered). The ion source consisted of a thin tungsten wire biased to 2 kV relative to two tungsten wire counter electrodes. Detection of ions was made by a sensitive current to voltage converter. Spectra were acquired by manually stepping the total voltage and recording the average ion current at each voltage step.

Figure 10A:
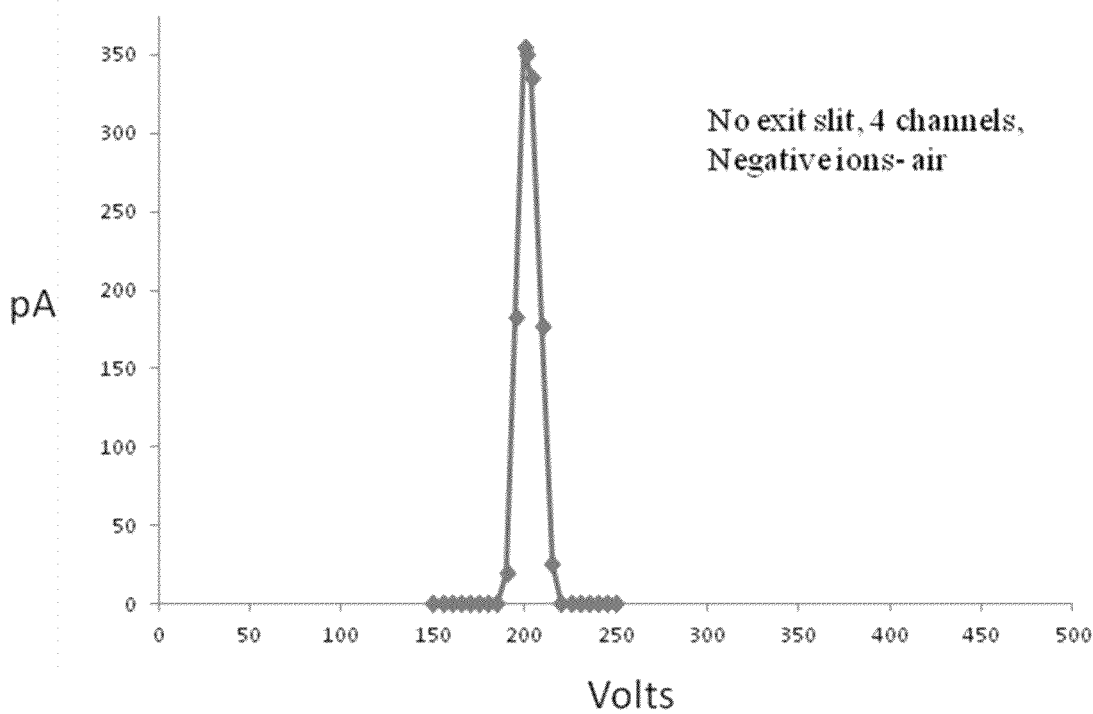
FIG. 10a shows an ion mobility spectrum obtained using a four channel prototype PFDMA sampling air ions formed in an electrical discharge with no exit slit.

Referring now to FIG. 10a, a spectrum of voltage versus ion intensity (inverse ion mobility versus ion intensity) is shown for background air ions in negative mode. One peak is present in the spectrum, most probably $O^-$ or $O_2^-$ or a small reactant product of these species; because the mobility is high (a low voltage is required to move the ions across the gas flow).

Figure 10B:
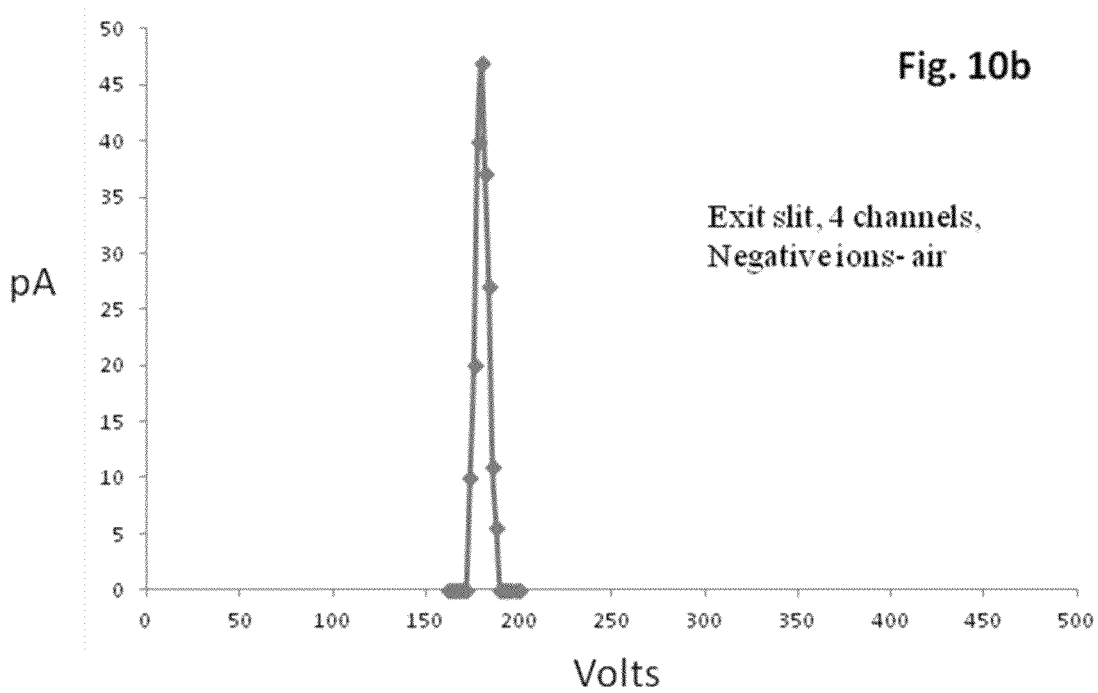
FIG. 10b shows an ion mobility spectrum obtained using a four channel prototype PFDMA sampling air ions formed in an electrical discharge with an exit slit.

When a small exit slit was added in front of the detector electrode the resulting spectrum resolution increased as shown in FIG. 10b.

An increase in resolution is expected as a slit allows only a narrow mobility range to reach the large detector electrode.

Figure 11A:
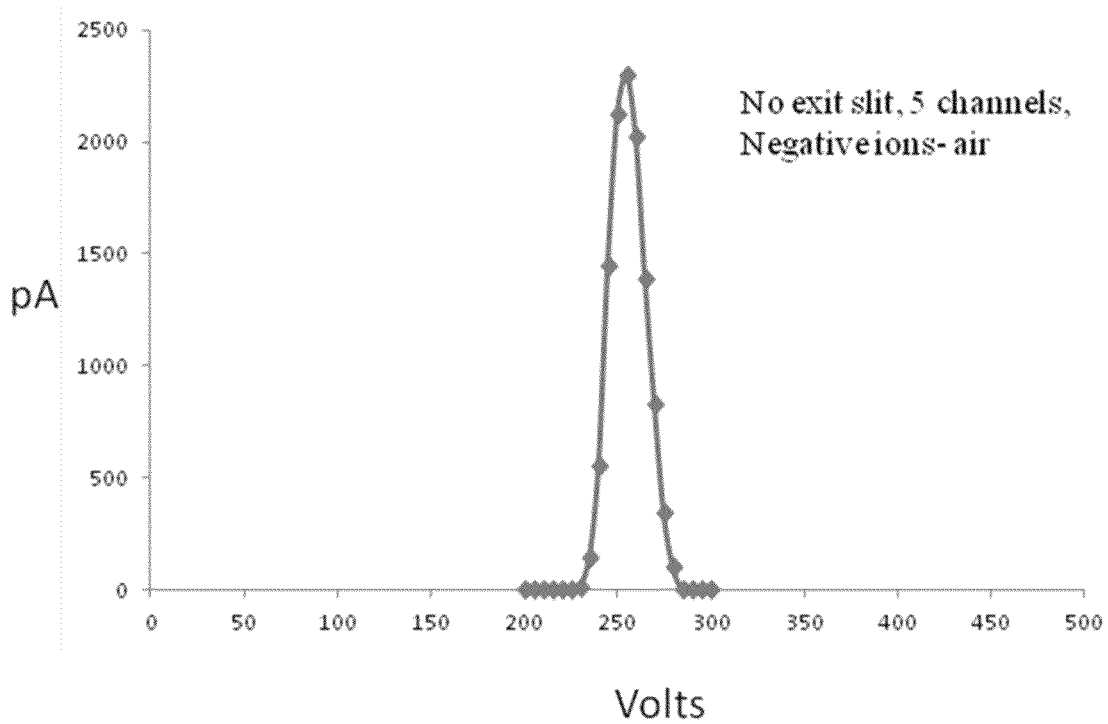
FIG. 11a shows an ion mobility spectrum obtained using a five channel prototype PFDMA sampling air ions formed in an electrical discharge with no exit slit. The device was operating in a high ion transmission mode producing an ion signal greater than two nano-amperes of current.

FIG. 11a shows a spectrum resulting when the number of channels is increased to five and the low side voltage is increase to 500V. In this case the device was optimized for high ion transmission as evidenced by the high ion current recorded, over two nanoamps.

Figure 11B:
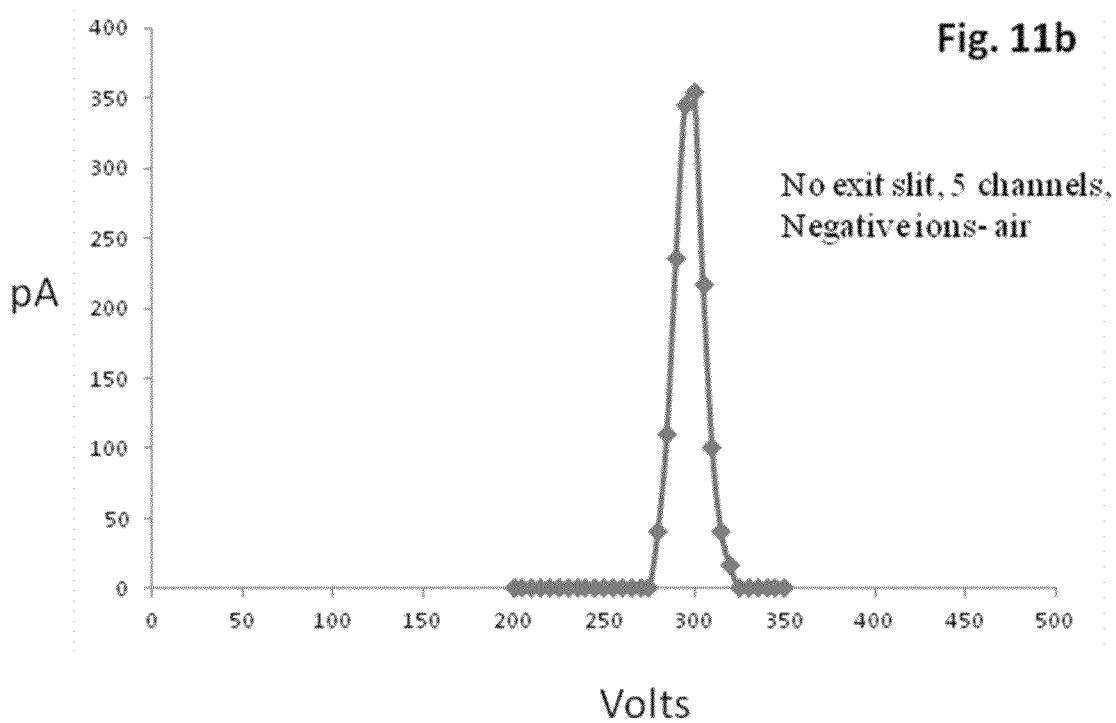
FIG. 11b shows an ion mobility spectrum obtained using a five channel prototype PFDMA sampling air ions formed in an electrical discharge with no exit slit. The device was operating in a higher resolution mode (higher voltage and higher gas velocity than shown in FIG. 11a).

FIG. 11b shows a spectrum obtained from the same five channel device when the gas flow rate is increased and the voltage sweep is also increased. As predicted the ion mobility distribution narrows and the resolution is increased. A further increase in resolution is possible by the addition of more channels, the introduction of an exit slit, or an increase in gas flow rate compensated with a higher electric field strength.

Example 2

A prototype PFDMA comprising a pair of six 0.50 mm channels separated by 0.50 mm was constructed. The arrangement was similar to the schematic shown in FIG. 3, i.e. in an inline mode. The gas flow was produced using a common vacuum cleaner connected to a rheostat to set the velocity, drawn in from the surrounding unfiltered laboratory air. The ion source consisted of a thin tungsten wire biased to 2 kV relative to two tungsten wire counter electrodes. Detection of ions was made by a sensitive current to voltage converter. Spectra were acquired by using a computer to simultaneously step the voltages of individual programmable high voltage power supplies connected to each electrode and recording the average ion current at each voltage step using an ADC board.

Figure 12A:
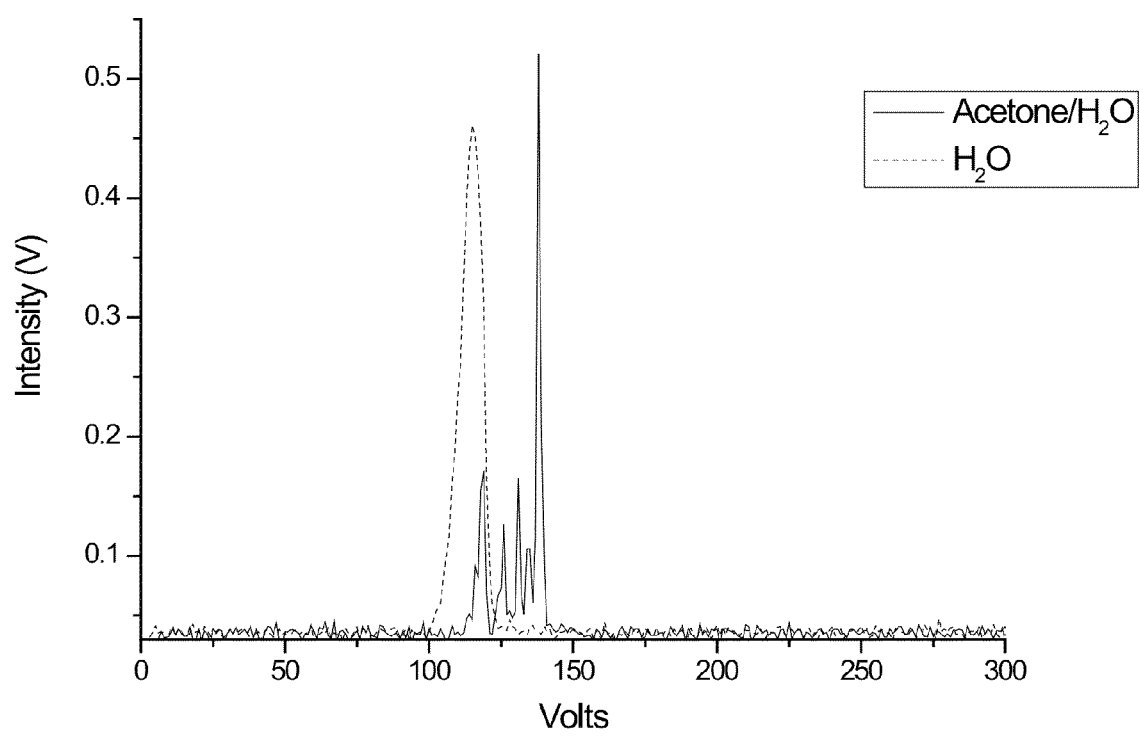
FIG. 12a shows an overlay ion mobility spectrum obtained using a six channel prototype PFDMA. Two ion mobility spectra were recorded with and without the addition of acetone vapor to room air under the same experimental conditions. Ten spectra were averaged every 20 ms in 1 volt steps over 300 volts, with low gas flow rate.

Referring now to FIG. 12a, an overlay spectrum of voltage versus ion intensity (inverse ion mobility versus ion intensity) is shown for background air ions (most probably clusters ions of $H_2O$) and product ions of acetone/$H_2O$ cluster ion reactions in positive mode. The mobility resolution was about 100, an increase relative to FIGS. 10 and 11 obtained by applying a more uniform retarding electric field.

Figure 12B:
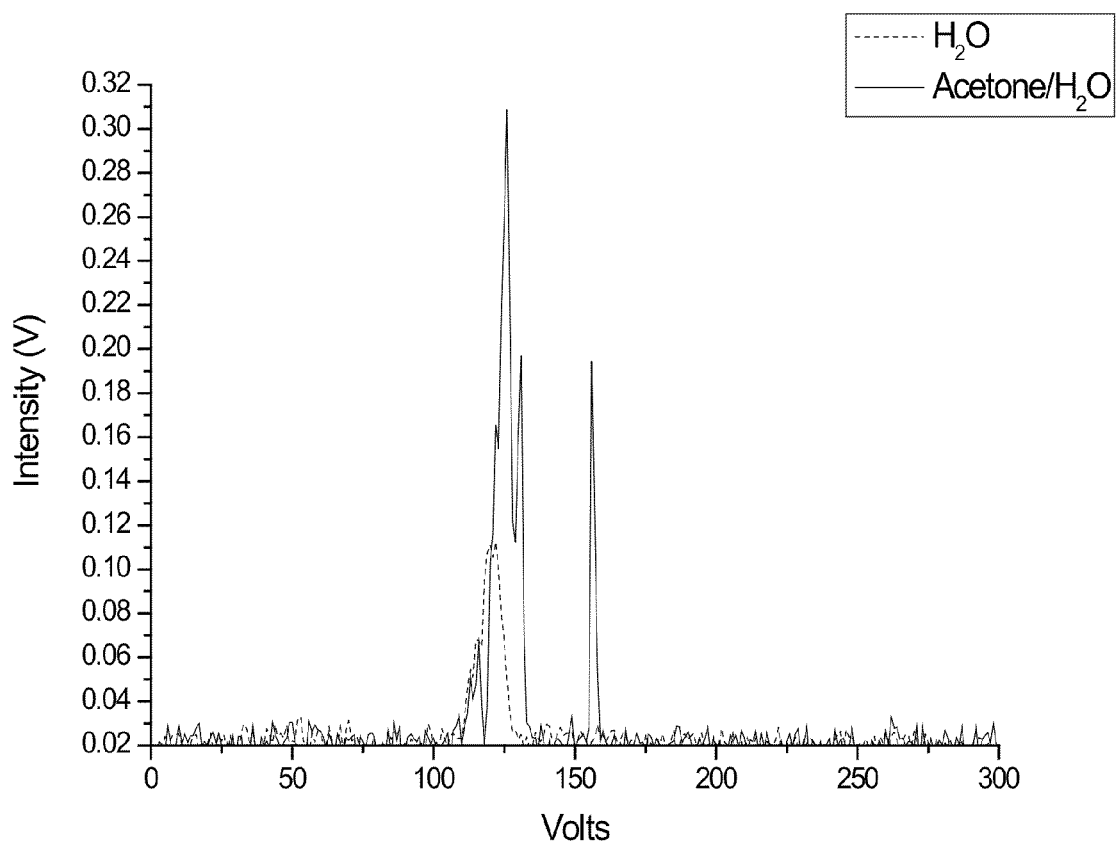
FIG. 12b shows an overlay ion mobility spectrum obtained using a six channel prototype PFDMA. The experimental conditions are similar to those used for obtaining FIG.

FIG. 12b shows an overlay spectrum for $H_2O$ ion clusters and acetone cluster ions when a longer reaction time produces larger cluster ions.

Figure 12C:
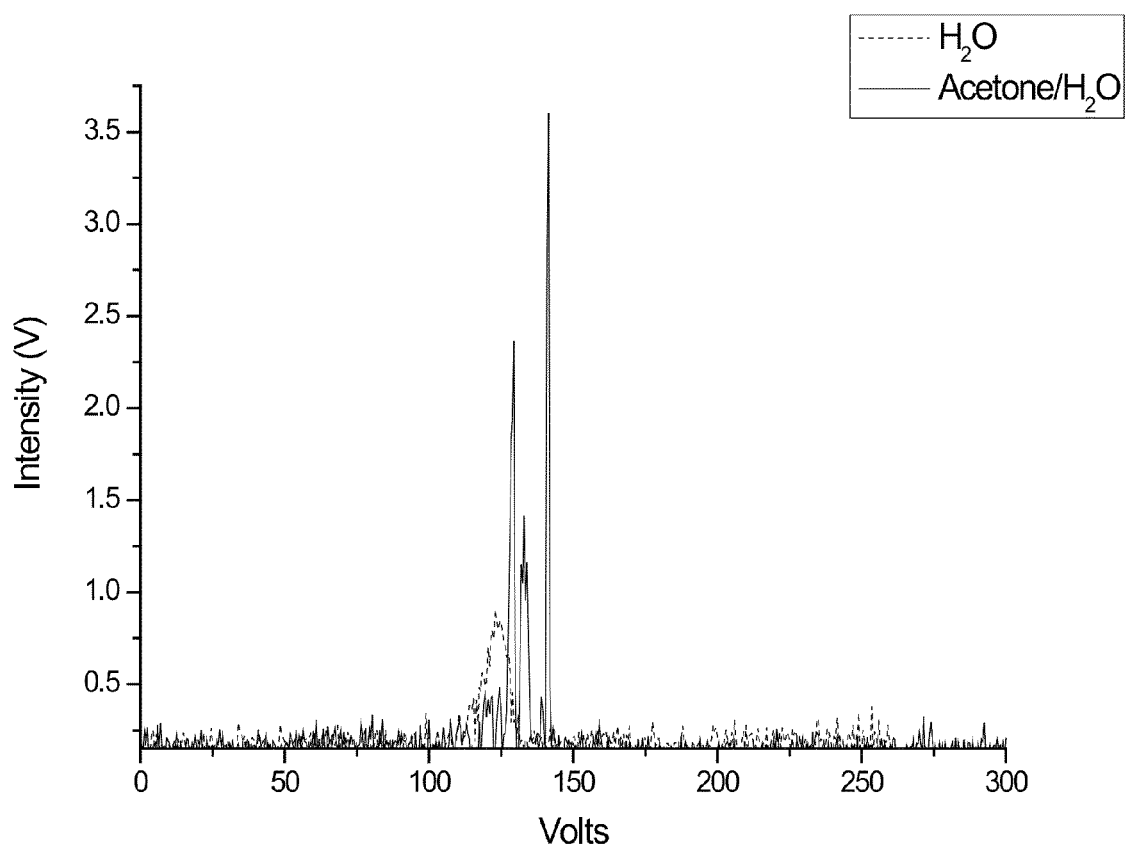

FIG. 12c shows an overlay spectrum for $H_2O$ ion clusters and acetone cluster ions recorded using a higher gas flow rate. The resolution of the acetone cluster ion peaks was about 145.

Figure 12D:
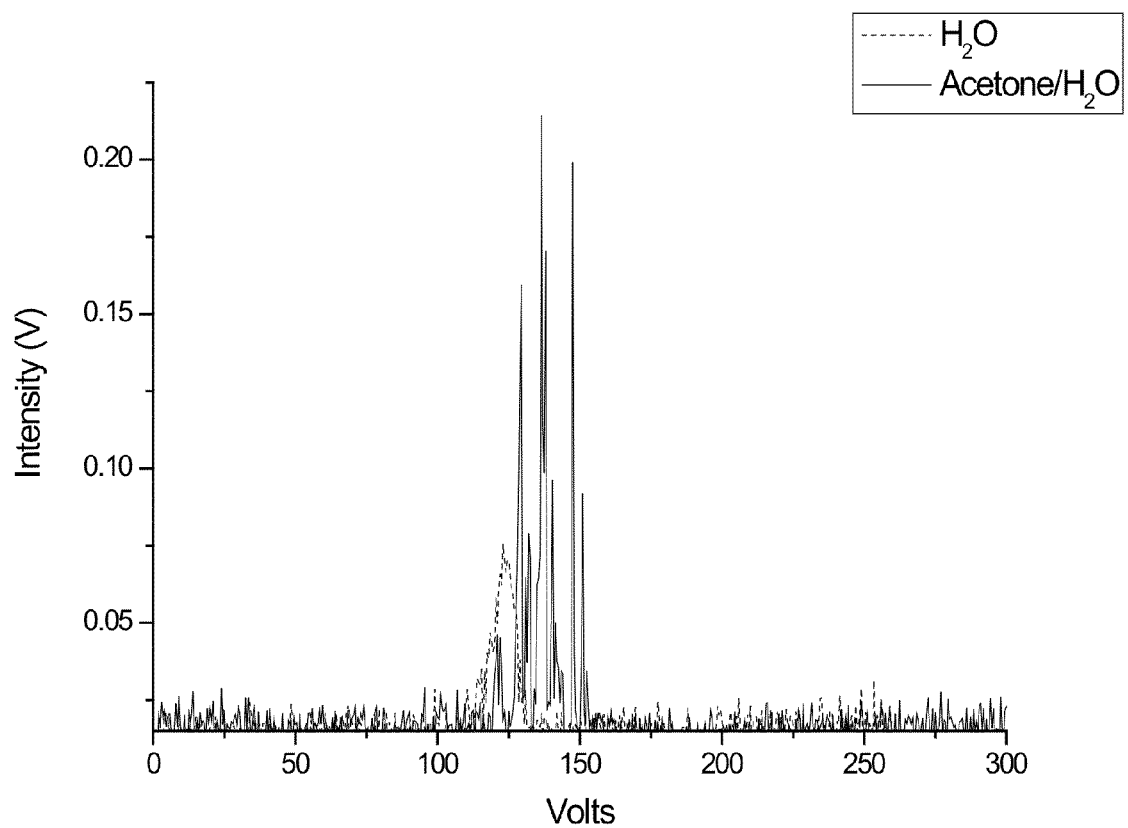
FIG. 12d shows an overlay ion mobility spectrum obtained using a six channel prototype PFDMA. The device was operating in a higher resolution mode, which was higher voltage and higher gas velocity than shown in FIG. 12a, with fewer ions allowed into the device than shown in FIG. 12c to increase resolution by limiting space charge effects.

FIG. 12d shows an overlay spectrum for $H_2O$ ion clusters and acetone cluster ions recorded when the ion source is restricted lowering the total ion current. The mobility resolution increased to about 230. This resolution is the highest ever reported to date for singly charged ions on any ion mobility spectrometer, DMA or drift tube.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described herein.

All publications and patents and literature specifically mentioned herein are incorporated by reference for all purposes. Nothing herein is to be construed as an admission that the invention is not entitled to antedate such disclosure by virtue of prior invention.

It is understood that this invention is not limited to the particular methodology, protocols, materials, and reagents described, as these may vary. It is also to be understood that the terminology used herein is for the purpose of describing particular embodiments only, and is not intended to limit the scope of the present invention which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A periodic field differential mobility analyzer apparatus for separating and identifying ionic analytes, comprising:
   a series of elongated parallel channels, each channel having an inlet at a first end and an outlet at a second end, each channel enclosed between first and second parallel walls, each first wall being formed from first and second electrode plates arranged to provide a slit opening in the first wall, each second wall being formed from third and fourth electrode plates arranged to provide a slit opening in the second wall, wherein the first and third electrode plates enclosing a channel oppose each other and the second and fourth electrode plates enclosing a channel oppose each other, wherein adjacent channels share electrode plates of one wall in common, wherein the channels are in fluid communication through the slit openings in each wall, and wherein the slit openings in each of the channels are aligned;
   a pump operable to force gas in laminar flow along each of the series of parallel channels, wherein the gas flows through and exits each channel separately and is not recirculated;
   a first voltage drop applied between the first and second electrode plates of the first wall of each channel providing an electric field $E_x$ in a direction opposing the gas flow, wherein the first voltage drop is also applied between the third and fourth electrode plates of the second wall;
   a second voltage drop applied between the first and third electrode plates of each channel providing an electric field $E_y$ in a direction perpendicular to the gas flow, wherein the second voltage drop is also applied between the second and fourth electrode plates of each channel, wherein the electric fields $E_x$ and $E_y$ form a periodic arrangement of their combined electric field and a retarding potential wall;
   an ion source arranged exterior to the channels for directing ionic analytes into an ion source slit of the wall of the channel farthest upstream with respect to the electric field $E_y$, wherein the path of the ionic analytes is linear along the channels until they reach the retarding potential wall; and
   a detector slit, wherein the detector slit is upstream from the ion source slit with respect to the direction of gas flow, and wherein the slit openings in each of the channels are aligned in a predetermined angle relative to the direction perpendicular to the walls of the channels so that the detector slit and the ion source slit are at opposite ends of the retarding potential wall.

2. The analyzer of claim 1, further comprising an exit slit in the wall of the channel farthest downstream with respect to the electric field $E_y$.

3. The analyzer of claim 1, further comprising maintaining the first and third electrode plates of each channel at ground potential so that the voltage drop applied between the first and third electrode plates is zero.

4. The analyzer of claim 1, wherein the number of channels in the series of elongated parallel channels is from two to fifty.

5. The analyzer of claim 1, wherein the first voltage drop can be swept from zero to 2000 volts.

6. The analyzer of claim 1, wherein the pump is operable to adjust the gas flow rate.

7. The analyzer of claim 1, wherein the pump is operable to adjust the gas flow rate from 0.1 to 2500 L/min.

8. The analyzer of claim 1, wherein the gas flow rates in each of the channels are equal.

9. The analyzer of claim 1, wherein the ion source generates ions by MALDI, electrospray ionization, laser ionization, thermospray ionization, thermal ionization, electron ionization, chemical ionization, inductively coupled plasma ionization, glow discharge ionization, field desorption ionization, fast atom bombardment ionization, spark ionization, or ion attachment ionization.

10. The analyzer of claim 1, wherein the ion source is a voltage biased tungsten wire.

11. The analyzer of claim 1, wherein the detector is a current to voltage converter, a gas amplification detector, a Daly detector, or a charge detector.

12. The analyzer of claim 1, wherein the analyzer achieves a resolution of greater than 100 with a transmission of greater than 90%.

13. The analyzer of claim 1, wherein the analyzer achieves a resolution of greater than 200 with a transmission of greater than 40%.

14. The analyzer of claim 1, wherein the analyzer achieves a resolution of greater than 50.

15. The analyzer of claim 1, wherein the analyzer achieves a resolution of greater than 75.

16. The analyzer of claim 1, wherein the analyzer achieves a resolution of greater than 100.

17. The analyzer of claim 1, wherein the analyzer achieves a resolution of greater than 200.

18. A mass spectrometer comprising an analyzer according to claim 1.

19. A periodic field differential mobility analyzer apparatus for separating and identifying ionic analytes, comprising:
   a series of differential mobility analyzers having channels arranged in parallel, wherein adjacent differential mobility analyzers share a common wall;
   a pump operable to force gas in laminar flow along the channels, wherein the gas flows through and exits each channel separately and is not recirculated;
   a first voltage drop applied to each differential mobility analyzer to provide an electric field $E_x$ in a direction opposing the gas flow;

a second voltage drop applied to each differential mobility analyzer to provide an electric field $E_y$ in a direction perpendicular to the gas flow, wherein the electric fields $E_x$ and $E_y$ form a periodic arrangement of their combined electric field and a retarding potential wall;

an ion source arranged exterior to the channels for directing ionic analytes through a slit of the wall of the channel farthest upstream with respect to the electric field $E_y$, wherein the path of the ionic analytes is linear along the channels until they reach the retarding potential wall; and a detector slit, wherein the detector slit is upstream from the ion source slit with respect to the direction of gas flow, and wherein the slit openings in each of the channels are aligned in a predetermined angle relative to the direction perpendicular to the walls of the channels so that the detector slit and the ion source slit are at opposite ends of the retarding potential wall.

20. The analyzer of claim 19, further comprising an exit slit in the channel farthest downstream with respect to the electric field $E_y$.

21. The analyzer of claim 19, wherein the number of channels is from two to twenty.

22. The analyzer of claim 19, wherein the first voltage drop can be swept from zero to 2000 volts.

23. The analyzer of claim 19, wherein the pump is operable to adjust the gas flow rate.

24. The analyzer of claim 19, wherein the pump is operable to adjust the gas flow rate from 0.1 to 2500 L/min.

25. The analyzer of claim 19, wherein the gas flow rates in each of the channels are equal.

26. The analyzer of claim 19, wherein the ion source generates ions by MALDI, electrospray ionization, laser ionization, thermospray ionization, thermal ionization, electron ionization, chemical ionization, inductively coupled plasma ionization, glow discharge ionization, field desorption ionization, fast atom bombardment ionization, spark ionization, or ion attachment ionization.

27. The analyzer of claim 19, wherein the ion source is a voltage biased tungsten wire.

28. The analyzer of claim 19, wherein the detector is a current to voltage converter, a gas amplification detector, a Daly detector, or a charge detector.

29. The analyzer of claim 19, wherein the analyzer achieves a resolution of greater than 100 with a transmission of greater than 90%.

30. The analyzer of claim 19, wherein the analyzer achieves a resolution of greater than 200 with a transmission of greater than 40%.

31. The analyzer of claim 19, wherein the analyzer achieves a resolution of greater than 50.

32. The analyzer of claim 19, wherein the analyzer achieves a resolution of greater than 75.

33. The analyzer of claim 19, wherein the analyzer achieves a resolution of greater than 100.

34. The analyzer of claim 19, wherein the analyzer achieves a resolution of greater than 200.

35. A mass spectrometer comprising an analyzer according to claim 19.

36. A method for separating and identifying ionic analytes, the method comprising:

providing a series of elongated parallel channels, each channel having an inlet at a first end and an outlet at a second end, each channel enclosed between first and second parallel walls, each first wall being formed from first and second electrode plates arranged to provide a slit opening in the first wall, each second wall being formed from third and fourth electrode plates arranged to provide a slit opening in the second wall, wherein the first and third electrode plates enclosing a channel oppose each other and the second and fourth electrode plates enclosing a channel oppose each other, wherein adjacent channels share electrode plates of one wall in common, wherein the channels are in fluid communication through the slit openings in each wall, and wherein the slit openings in each of the channels are aligned;

operating a pump to force gas in laminar flow along each of the series of parallel channels, wherein the gas flows through and exits each channel separately and is not recirculated;

applying a first voltage drop between the first and second electrode plates of the first wall of each channel providing an electric field $E_x$ in a direction opposing the gas flow, wherein the first voltage drop is also applied between the third and fourth electrode plates of the second wall;

applying a second voltage drop between the first and third electrode plates of each channel providing an electric field $E_y$ in a direction perpendicular to the gas flow, wherein the second voltage drop is also applied between the second and fourth electrode plates of each channel, wherein the electric fields $E_x$ and $E_y$ form a periodic arrangement of their combined electric field and a retarding potential wall;

directing ionic analytes from an ion source into an ion source slit of the wall of the channel farthest upstream with respect to the electric field $E_y$, wherein the path of the ionic analytes is linear along the channels until they reach the retarding potential wall; and detecting the ionic analytes, wherein a detector slit is upstream from the ion source slit with respect to the direction of gas flow, and wherein the slit openings in each of the channels are aligned in a predetermined angle relative to the direction perpendicular to the walls of the channels so that the detector slit and the ion source slit are at opposite ends of the retarding potential wall.

* * * * *